United States Patent
Adler et al.

(10) Patent No.: US 11,116,478 B2
(45) Date of Patent: Sep. 14, 2021

(54) DIAGNOSIS OF PATHOLOGIES USING INFRASONIC SIGNATURES

(71) Applicant: Bat Call D. Adler Ltd., Nesher (IL)

(72) Inventors: Doron Adler, Haifa (IL); Igor Kagan, Kiriat Bialik (IL); Ezra Salomon, Rakefet (IL); Omri Adler, Haifa (IL); David Linhard, Haifa (IL); Hod Gilad, Haifa (IL)

(73) Assignee: SANOLLA LTD., Nesher (IL)

( * ) Notice: Subject to any disclaimer, the term of this patent is extended or adjusted under 35 U.S.C. 154(b) by 459 days.

(21) Appl. No.: 15/953,502

(22) Filed: Apr. 16, 2018

(65) Prior Publication Data
US 2018/0228468 A1 Aug. 16, 2018

Related U.S. Application Data

(63) Continuation-in-part of application No. PCT/IB2017/050833, filed on Feb. 15, 2017.
(Continued)

(51) Int. Cl.
*A61B 8/00* (2006.01)
*H04R 29/00* (2006.01)
(Continued)

(52) U.S. Cl.
CPC ............ *A61B 8/461* (2013.01); *A61B 5/7415* (2013.01); *A61B 7/003* (2013.01); *A61B 7/04* (2013.01);
(Continued)

(58) Field of Classification Search
CPC .. A61B 7/04; A61B 7/003; H04R 1/46; G06F 17/14
See application file for complete search history.

(56) References Cited

U.S. PATENT DOCUMENTS 3,433,959 A 3/1969 Atwood et al.
3,580,082 A 5/1971 Strack et al.
(Continued)

FOREIGN PATENT DOCUMENTS

CN 103479385 A 1/2014
CN 103479386 A 1/2014
(Continued)

OTHER PUBLICATIONS

European Application #17752765.2 search report dated Oct. 8, 2019.
(Continued)

*Primary Examiner* — Christian Jang
*Assistant Examiner* — Karen E Toth
(74) *Attorney, Agent, or Firm* — Kligler & Associates Patent Attorneys Ltd

(57) ABSTRACT

A medical device includes an acoustic transducer, which is configured to sense infrasonic waves emitted from a body of a living subject with a periodicity determined by a periodic physiological activity and to output an electrical signal in response to the sensed waves. At least one speaker is configured to output audible sounds in response to an electrical input. Processing circuitry is configured to process the electrical signal so as to generate a frequency-stretched signal in which infrasonic frequency components of the electrical input are shifted to audible frequencies while preserving the periodicity of the periodic physiological activity in the frequency-stretched signal, and to input the frequency-stretched signal to the at least one speaker.

7 Claims, 10 Drawing Sheets

Related U.S. Application Data

(60) Provisional application No. 62/554,041, filed on Sep. 5, 2017, provisional application No. 62/296,113, filed on Feb. 17, 2016.

(51) Int. Cl.

| | | |
|---|---|---|
| *A61B 5/00* | (2006.01) | |
| *A61B 7/00* | (2006.01) | |
| *A61B 8/08* | (2006.01) | |
| *A61B 7/04* | (2006.01) | |
| *A61B 5/113* | (2006.01) | |
| *A61B 5/08* | (2006.01) | |

(52) U.S. Cl.
CPC ............. *A61B 8/08* (2013.01); *A61B 8/4416* (2013.01); *A61B 8/4483* (2013.01); *A61B 8/5223* (2013.01); *H04R 29/008* (2013.01); *A61B 5/0816* (2013.01); *A61B 5/113* (2013.01); *A61B 5/7246* (2013.01)

(56) References Cited

U.S. PATENT DOCUMENTS

| | | | |
|---|---|---|---|
| 4,792,145 A * | 12/1988 | Eisenberg | A61B 7/04 381/67 |
| 5,301,679 A | 4/1994 | Taylor | |
| 5,853,005 A | 12/1998 | Scanlon | |
| 6,154,551 A | 11/2000 | Frenkel | |
| 6,520,924 B2 | 2/2003 | Lee | |
| 6,699,204 B1 | 3/2004 | Kehyayan et al. | |
| 6,778,673 B1 | 8/2004 | Hobelsberger | |
| 6,788,417 B1 | 9/2004 | Zumberge et al. | |
| 7,458,939 B2 | 12/2008 | Munk | |
| 7,976,480 B2 | 7/2011 | Grajales et al. | |
| 8,015,878 B2 | 9/2011 | Melikechi et al. | |
| 8,419,652 B2 | 4/2013 | Rajamani et al. | |
| 8,475,396 B2 | 7/2013 | Jones et al. | |
| 8,920,343 B2 | 12/2014 | Sabatino | |
| 9,101,274 B2 | 8/2015 | Bakema et al. | |
| 9,277,330 B2 | 3/2016 | Aharoni et al. | |
| 9,345,432 B2 | 5/2016 | Salisbury et al. | |
| 9,445,779 B2 | 9/2016 | Shams et al. | |
| 10,842,416 B2 | 11/2020 | Joseph et al. | |
| 10,881,330 B2 | 1/2021 | Joseph et al. | |
| 2001/0030077 A1 | 10/2001 | Watson | |
| 2002/0071570 A1 | 6/2002 | Cohen et al. | |
| 2002/0183642 A1 | 12/2002 | Murphy | |
| 2003/0002685 A1 | 1/2003 | Werblud | |
| 2004/0260193 A1 | 12/2004 | LaSala | |
| 2005/0222515 A1 | 10/2005 | Polyshchuk et al. | |
| 2005/0273015 A1 | 12/2005 | Bauer et al. | |
| 2006/0070623 A1 | 4/2006 | Wilkinson et al. | |
| 2007/0050715 A1 | 3/2007 | Behar | |
| 2007/0058818 A1 | 3/2007 | Yoshimine | |
| 2008/0013747 A1 | 1/2008 | Tran | |
| 2009/0316925 A1 * | 12/2009 | Eisenfeld | A61B 7/008 381/67 |
| 2011/0137209 A1 | 6/2011 | Lahiji et al. | |
| 2011/0222697 A1 | 9/2011 | Dong et al. | |
| 2011/0224988 A1 | 9/2011 | Mahajan et al. | |
| 2012/0209132 A1 * | 8/2012 | Jones | G01S 5/18 600/528 |
| 2013/0041278 A1 | 2/2013 | Bai et al. | |
| 2014/0073864 A1 | 3/2014 | Engelbrecht et al. | |
| 2014/0155762 A1 * | 6/2014 | Maskara | A61B 7/003 600/484 |
| 2014/0290372 A1 | 10/2014 | Lagaros et al. | |
| 2015/0073306 A1 | 3/2015 | Abeyratne et al. | |
| 2015/0119758 A1 | 4/2015 | Rogers et al. | |

FOREIGN PATENT DOCUMENTS

| | | |
|---|---|---|
| CN | 203506748 U | 4/2014 |
| CN | 107510473 A | 12/2017 |
| DE | 202005006661 U1 | 8/2005 |
| KR | 20120040530 A | 4/2012 |
| WO | 9325874 A1 | 12/1993 |
| WO | 0002486 A1 | 1/2000 |
| WO | 2002009586 A2 | 2/2002 |
| WO | 2006075263 A1 | 7/2006 |
| WO | 2011117862 A2 | 9/2011 |
| WO | 2014163443 A1 | 10/2014 |
| WO | 2015157458 A1 | 10/2015 |
| WO | 2016113562 A1 | 7/2016 |
| WO | 2017141165 A1 | 8/2017 |

OTHER PUBLICATIONS

International Application #PCT/IB2018/056335 search report dated Dec. 26, 2018.
International Application #PCT/IB2018/056336 search report dated Dec. 25, 2018.
Kirgizov., U.S. Appl. No. 29/630,202, filed Dec. 20, 2017.
Padmanabhan et al., "Accelerometer type cardiac transducer for detection of low-level heart sounds", IEEE Transactions on Biomedical Engineering, vol. 40, No. 1, pp. 21-28, Jan. 1, 1993.
International Application #PCT/IB2017/050833 search report dated Jul. 23, 2017.
Bukhman et al., "Spectral analysis of acoustic vibrations on the surface of the human body," Acoustical Physics, vol. 41, Issue 1, 10 pages, 1995.
European Application #20168052.7 Search Report dated Jun. 29, 2020.
EP Application # 18853978.7 Search Report dated Apr. 22, 2021.
EP Application # 18855091.7 Search Report dated Apr. 22, 2021.

\* cited by examiner

DIAGNOSIS OF PATHOLOGIES USING INFRASONIC SIGNATURES

CROSS-REFERENCE TO RELATED APPLICATIONS

This application claims the benefit of U.S. Provisional Patent Application 62/554,041, filed Sep. 5, 2017, which is incorporated herein by reference. This application is also a continuation in part of PCT Patent Application PCT/IB2017/050833, filed Feb. 15, 2017, which claims the benefit of U.S. Provisional Patent Application 62/296,113, filed Feb. 17, 2016. All of these related applications are incorporated herein by reference.

FIELD OF THE INVENTION

The present invention relates generally to methods, apparatus and software for medical diagnosis, and particularly to techniques for diagnosis of medical conditions based on processing of acoustic signals.

BACKGROUND

Auscultation has been a key technique in medical diagnosis for centuries. In auscultation, the medical practitioner listens to the internal sounds of the body, typically using a stethoscope. Auscultation is most commonly performed for the purpose of examining the circulatory and respiratory systems, and thus diagnosing conditions of the heart and lungs in particular. In more recent years, electronic stethoscopes and methods of digital processing of body sounds have become available, in order to enhance and supplement the practitioner's auditory capabilities.

For example, U.S. Pat. No. 5,853,005 describes an acoustic monitoring system in which a transducer in communication with fluid in a pad is held in close contact against a sound or movement source and monitors acoustic signals transferred into the fluid. The signal pattern is monitored aurally and/or compared to predetermined reference patterns.

As another example, U.S. Pat. No. 6,699,204 describes a device for analyzing auscultation sounds, in particular respiratory sounds. The device comprises an input receiving a sound signal sampled in intensity levels each associated with a selected time, and storage means comprising a processing module for evaluating, in cooperation with computing means, a set of transformed intensity levels, each associated with a predetermined sound frequency. It further comprises an output connected to the storage means for delivering each transformed intensity level in correspondence with an associated frequency, and means for representing intensity levels transformed on the basis of frequencies, to obtain a spectral representation of the auscultation sound.

U.S. Patent Application Publication 2005/0222515 describes methods of analyzing patient's heart, using a cardiovascular sound signature in diagnosis at the early stages of cardiac dysfunctions. The invention is said to present cardiovascular sounds in time and frequency while keeping signal resolution equally strong in both directions.

SUMMARY

Embodiments of the present invention that are described hereinbelow provide methods, apparatus and software for processing and analysis of acoustic signals received from the body.

There is therefore provided, in accordance with an embodiment of the invention, a medical device, including an acoustic transducer, which is configured to sense infrasonic waves emitted from a body of a living subject with a periodicity determined by a periodic physiological activity and to output an electrical signal in response to the sensed waves. At least one speaker is configured to output audible sounds in response to an electrical input. Processing circuitry is configured to process the electrical signal so as to generate a frequency-stretched signal in which infrasonic frequency components of the electrical input are shifted to audible frequencies while preserving the periodicity of the periodic physiological activity in the frequency-stretched signal, and to input the frequency-stretched signal to the at least one speaker.

In some embodiments, the processing circuitry is configured to receive and digitize the electrical signal, to transform the digitized signal to a frequency domain, to shift the infrasonic frequency components to the audible frequencies in the frequency domain so as to generate a frequency-shifted transformed signal, and to retransform the frequency-shifted transformed signal to a time domain in order to generate the frequency-stretched signal. In a disclosed embodiment, the processing circuitry is configured to shift the infrasonic frequency components by interpolating the transformed signal by a predefined factor, and to decimate the retransformed signal in the time domain by the predefined factor in order to generate the frequency-stretched signal while preserving the periodicity of the periodic physiological activity.

In some embodiments, the device includes a user interface, which is configured to receive a user input from a user of the device indicative of a desired stretch of the infrasonic frequency components, and the processing circuitry is configured to adjust the predefined factor responsively to the user input. The user interface can be configured to select a value of the predefined factor from among a first value for transformation of respiratory sounds and a second value, greater than the first value, for transformation of cardiac sounds.

In a disclosed embodiment, the infrasonic frequency components sensed by the acoustic transducer have frequencies extending at least down to 5 Hz, and the processing circuitry is configured to stretch the infrasonic frequency components so that a component at 5 Hz is shifted to a frequency of at least 20 Hz.

In one embodiment, the device includes a case, which contains the acoustic transducer and at least a part of the processing circuitry, and which is configured to be brought into contact with the body of the living subject, wherein the at least one speaker includes earphones extending from the case and configured to configured to output the audible sounds.

There is also provided, in accordance with an embodiment of the invention, a medical device, including an acoustic transducer, which is configured to sense acoustic waves emitted from a body of a living subject in response to a periodic physiological activity and to output an electrical signal in response to the sensed waves. Processing circuitry is configured to compute respective autocorrelations of the electrical signal for a plurality of different times within a period of the physiological activity, to transform the respective autocorrelations to a frequency domain, and to render to a display, responsively to the transformed autocorrelations, a graphical representation of a spectral distribution of an energy of the acoustic waves over the period.

In some embodiments, the acoustic waves include an infrasonic component, and the spectral distribution includes the energy at infrasonic frequencies. In one embodiment, the device includes at least one speaker, which is configured to output audible sounds in response to an electrical input, wherein the processing circuitry is configured to shift the infrasonic component to audible frequencies so as to generate a frequency-stretched signal, and to generate the electrical input to the at least one speaker responsively to the frequency-stretched signal.

In some embodiments, the physiological activity includes respiration, and the graphical representation is indicative of the energy of the acoustic waves due to respiratory activity of the body. In a disclosed embodiment, the device includes a motion sensor and a case, which contains the acoustic transducer and the motion sensor and is configured to be brought into contact with the body of the living subject, wherein the processor is configured to detect a respiratory motion responsively to an output of the motion sensor, and to extract the period of the respiratory activity from the detected respiratory motion.

Typically, the graphical representation includes a plot having a frequency axis and a time axis defining a time-frequency plane and presenting a value of the energy at each point in the time-frequency plane.

There is additionally provided, in accordance with an embodiment of the invention, a method for medical diagnosis, which includes receiving an electrical signal from an acoustic transducer in response to infrasonic waves emitted from a body of a living subject with a periodicity determined by a periodic physiological activity. The electrical signal is processed so as to generate a frequency-stretched signal in which infrasonic frequency components of the electrical input are shifted to audible frequencies while preserving the periodicity of the periodic physiological activity in the frequency-stretched signal. An electrical input to at least one speaker is generated responsively to the frequency-stretched signal, whereby the at least one speaker outputs audible sounds in response to the electrical input.

There is further provided, in accordance with an embodiment of the invention, a method for medical diagnosis, which includes receiving an electrical signal from an acoustic transducer in response to acoustic waves emitted from a body of a living subject due to a periodic physiological activity. Respective autocorrelations of the electrical signal are computed for a plurality of different times within a period of the physiological activity. The respective autocorrelations are transformed to a frequency domain, and responsively to the transformed autocorrelations, a graphical representation of a spectral distribution of an energy of the acoustic waves over the period is rendered to a display.

The present invention will be more fully understood from the following detailed description of the embodiments thereof, taken together with the drawings in which:

DETAILED DESCRIPTION OF EMBODIMENTS

Overview

Figure 1:
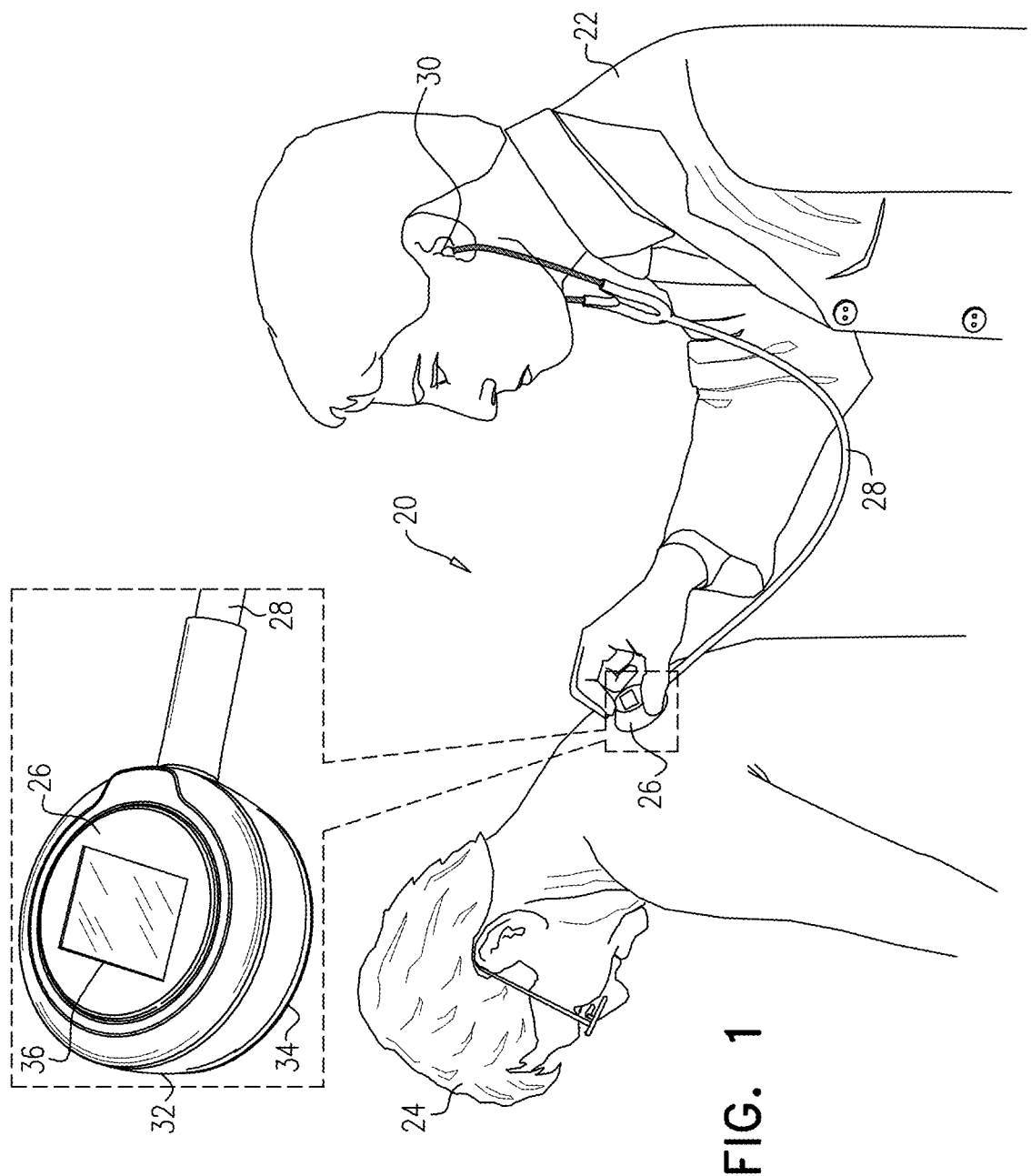
FIG. 1 is a schematic pictorial illustration showing a digital stethoscope in clinical use, in accordance with an embodiment of the invention.

The stethoscope is generally the first tool that the medical practitioner deploys in attempting to diagnose conditions of the circulatory and respiratory systems. Stethoscopes that are known in the art, however, including electronic stethoscopes, are limited by the user's auditory capabilities and diagnostic skills. Acoustic vibrations generated by physiological activity contain a wealth of diagnostic information that is not exploited by traditional auscultation.

Embodiments of the present invention that are described herein address these limitations by applying techniques of digital signal processing to acoustic waves that are emitted from the body of a living subject in response to periodic physiological activities, such as heart motion and respiration. These embodiments provide processing circuitry and methods that can be incorporated, for example, into a digital electronic stethoscope, or alternatively used in conjunction with acoustic transducers in other sorts of diagnostic devices and systems (such as those described in the above-mentioned PCT Patent Application PCT/IB2017/050833). The disclosed embodiments take advantage not only of acoustic waves in the audible range (defined as the range between 20 Hz and 20,000 Hz), but also infrasonic waves, at frequencies below 20 Hz.

In some embodiments, the processing circuitry processes electrical signal output by an acoustic transducer so as to generate a frequency-stretched signal, in which infrasonic frequency components of the electrical input are shifted to audible frequencies. Although the signal frequencies are shifted, however, the periodicity of the periodic physiological activity is preserved in the frequency-stretched signal. Consequently, the heart sounds repeat at the original heart rate, and breath sounds repeat at the original respiratory rate, while the infrasonic components (as well as audible components) are shifted to higher tones in the audible range.

The processing circuitry inputs the frequency-stretched signal to one or more speakers, such as the earphones of an electronic stethoscope, which output the corresponding audible sounds. The medical practitioner can use such a device intuitively, as he or she would use a conventional stethoscope, but will be able to hear a wealth of additional sounds (with the expected periodicity) indicative of infrasonic activity. The inventors have found that this approach enhances the practitioner's ability to diagnose cardiac and pulmonary pathologies with only a short learning curve.

In other embodiments, the processing circuitry computes and displays acoustic "signatures" based on the electrical signal output by the acoustic transducer. Such signatures may be applied in conjunction with or separately from the frequency-stretching techniques described above. Specifically, to accommodate the periodic nature of the physiological activity, the processing circuitry computes respective autocorrelations of the electrical signal at multiple different times within the period of the physiological activity. The separation between the autocorrelation peaks reflects the period, for example, the respiratory period, while the autocorrelation amplitude reflects the energy content of the signal.

The processing circuitry transforms the autocorrelation curves to the frequency domain, and renders the transformed autocorrelations in graphical form to a display. This display presents a spectral distribution of the energy of the acoustic waves over the period of the physiological activity, showing how the pattern of frequencies (including infrasonic frequencies) changes over the period, for example over the course of a respiratory cycle. The inventors have found that certain respiratory pathologies are characterized by distinct spectral patterns, referred to as signatures, some of which are illustrated in the figures that follow. Because the autocorrelation function reflects the actual, natural period of the physiological activity, as opposed to computing signal energy over some other, arbitrary window, the acoustic signature based on the autocorrelation provides a self-consistent, intuitive picture of the activity and associated pathologies.

System Description

FIG. 1 is a schematic pictorial illustration showing the use of a digital stethoscope 20, in accordance with an embodiment of the invention. A practitioner 22 brings a head 26 of stethoscope 20 into contact with the body of a patient 24. Processing circuitry in head 26 outputs an audio signal via a cable 28 extending from head 26 to one or more speakers, such as earphones 30, which open apart and fit into the practitioner's ears as would the earphones of a conventional stethoscope.

As shown in the inset, head 26 comprises a case 32, which contains an acoustic transducer, such as a suitable microphone 34, which contacts the body of patient 24 and thus senses acoustic waves emitted from the body. Microphone 34 may be of any suitable type that is known in the art, for example a piezoelectric sensor, which is sensitive not only to audible frequencies, but also to infrasonic frequencies going down to 5 Hz. On the other side of head 26, a user interface, such as a touch-sensitive display 36, enables practitioner 22 to control the functions of stethoscope 20 and displays data, such as acoustic signatures of heart and/or breath sounds sensed by microphone 34.

Figure 2:
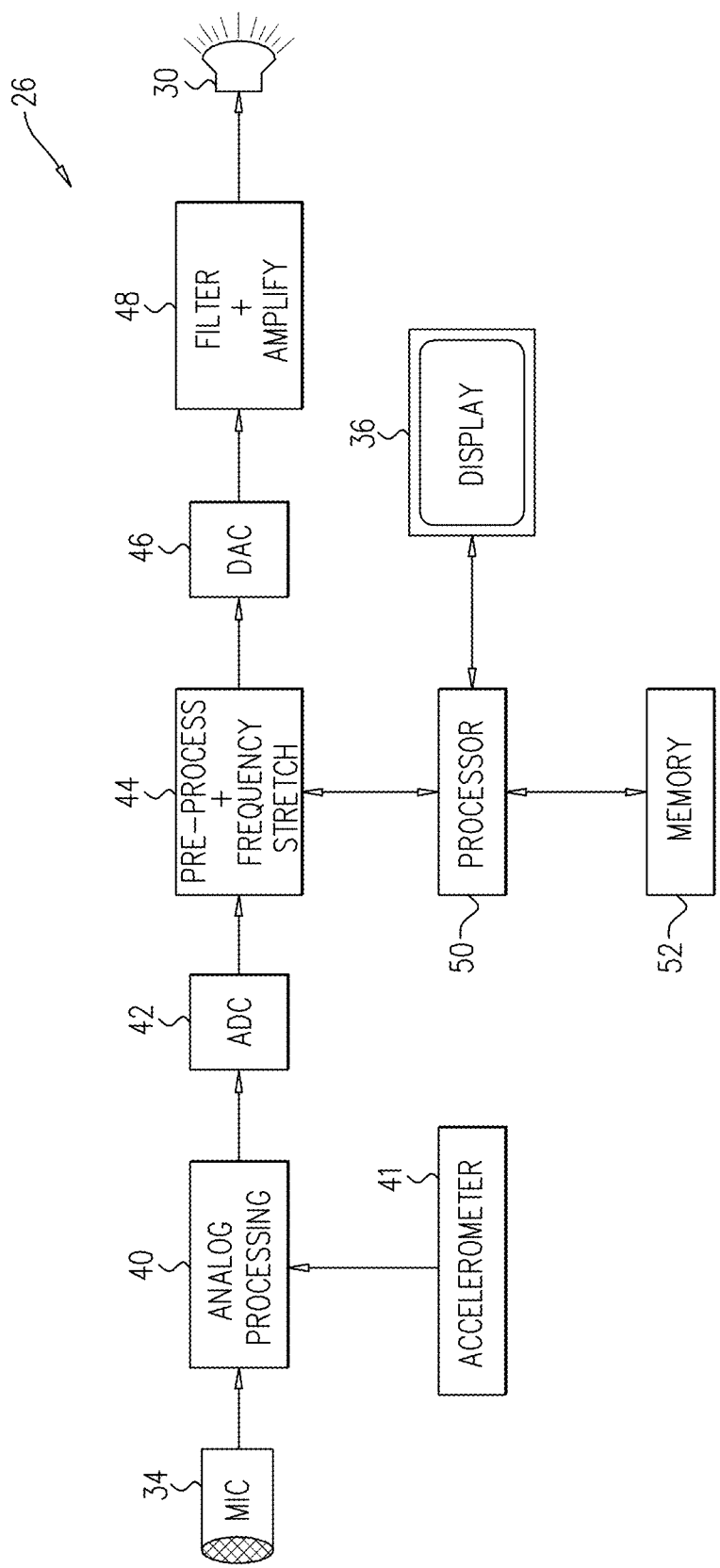
FIG. 2 is a block diagram that schematically shows elements of a digital stethoscope, in accordance with an embodiment of the invention.

FIG. 2 is a block diagram that schematically shows functional elements of stethoscope 20, in accordance with an embodiment of the invention. In the pictured embodiment, the elements shown in FIG. 2 are assumed to be contained inside head 26, within case 32. Alternatively, however, some of these components may be housed in an external processing unit.

An analog front end 40 performs analog processing functions, including filtering, buffering and amplification of the electrical signals output by microphone 34. Optionally, head 26 also comprises an inertial sensor, such as an integrated circuit accelerometer 41, which measures motion and low-frequency vibrations of head 26. Analog front end 40 may then process the signals output by the inertial sensor, as well. An analog/digital converter (ADC) 42 digitizes the acoustic and inertial signals.

A digital preprocessing circuit 44 transforms the digitized signals to the frequency domain, for example by computing a short-time Fourier transform (SIFT) over successive time windows of the signals. In addition, circuit 44 can perform digital filtering functions, such as noise suppression, and "frequency stretching": shifting infrasonic frequency components to the audible frequency range, as described further hereinbelow. Following these filtering and frequency stretching steps, circuit 44 converts the frequency-domain samples back to the time domain. For these purposes, circuit 44 typically comprises digital processing logic, which may be hard-wired or programmable; but alternatively, at least some of the functions of circuit 44 may be carried out on a programmable processor under the control of software or firmware. A digital/analog converter (DAC) converts the stream of time-domain samples to analog form. An analog output circuit 48 filters and amplifies the analog signal to generate an electrical input to earphones 30.

A programmable processor 50 receives the stream of samples—in either the time domain or the frequency domain, or both—from digital preprocessing circuit 44. Processor 50 is coupled to a memory 52, which typically comprises non-volatile memory, such as flash memory, containing software or firmware to control the operations of processor 50. In addition, memory 52 typically comprises volatile random-access memory (RAM), which is used by processor 50 to store the digital samples received from circuit 44, as well as processing results.

Based on the digitized samples, processor 50 can compute acoustic signatures, representing the spectral distribution of the energy of the acoustic waves over the period of the cardiac or respiratory cycle, as described further hereinbelow. Processor 50 renders a graphical representation of the acoustic signature to display 36 and/or outputs the signature information via a communication link (not shown). In addition, processor may receive and carry out user instructions, for example in response to finger gestures on the touch screen of display 36.

The processing components shown FIG. 2, including analog front end 40, ADC 42, digital preprocessing circuit 44, DAC 46, analog output circuit 48, processor and memory 52, are collectively and individually referred to herein as "processing circuitry." These components are typically implemented in integrated circuits, as are known in the art, which are mounted together on a printed circuit board within case 32. Alternatively, other implementations of these functional components will be apparent to those skilled in the art after reading the present description and are considered to be within the scope of the present invention. Although FIG. 2 shows a certain arrangement of functional blocks for the sake of conceptual clarity, the functions of at least some of these blocks may be combined into a single integrated circuit chip or, alternatively, split among multiple chips.

Frequency Stretching of Infrasonic Signals

Figure 3:
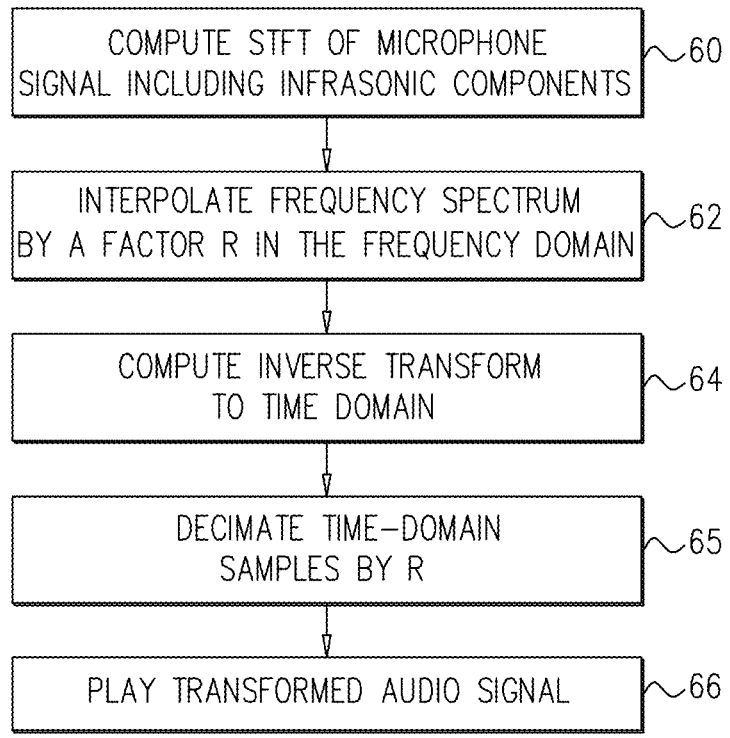
FIG. 3 is a flow chart that schematically illustrates a method for frequency stretching of infrasonic signals, in accordance with an embodiment of the invention.

FIG. 3 is a flow chart that schematically illustrates a method for frequency stretching of infrasonic signals, in accordance with an embodiment of the invention. The method is described here, for the sake of concreteness and clarity, with reference to the components of digital stethoscope 20. As noted earlier, the object of this method is to generate a frequency-stretched signal in which infrasonic frequency components of the electrical input from microphone 34 are shifted to audible frequencies, while preserving the periodicity of periodic physiological activities (such as heartbeat and/or respiration) in the frequency-stretched signal. Digital preprocessing circuit 44 generates the frequency-stretched signal in real time, for output via earphones 30. Alternatively, the principles of the method of FIG. 3 may be implemented in substantially any system that includes a suitable acoustic transducer, speaker and processing resources.

In the method of FIG. 3, analog front end 40 receives the electrical signal output by microphone 34, and ADC 42 digitizes the signal. The time-domain digital samples are input to digital preprocessing circuit 44, which transforms the digitized signal to the frequency domain, using a short-time Fourier transform (STFT), for example. Formally, the STFT F(m,k) of the time-domain signal f[n], is computed by applying the formula:

$$F(m,k) = \Sigma_n f[n] * w[n-m] e^{-jkn}$$

Here m and k are both discrete variables (m being the time variable and k being the frequency variable), and w[n] is a suitable window function, such as a Hamming, Gaussian, or Hann window function.

Next, circuit 44 interpolates the frequency spectrum F(m, k) in the frequency domain by a factor R in order to yield interpolated spectrum $F_r(m,k)$, in which the infrasonic components are shifted to audible frequencies, at an interpolation step 62. Generally speaking, R may take any rational value, but typical values of R are in the range between 2 and 20, in order to shift infrasonic frequency components to the low end of the audible range. Assuming that the infrasonic frequency components sensed by microphone 34 have frequencies extending at least down to 5 Hz, and circuit 44 will use a value of R such that the infrasonic frequency component at 5 Hz will be shifted to a frequency of at least 20 Hz.

Different values of R can be used depending upon whether practitioner 22 wishes to hear respiratory or cardiac sounds. For example, respiratory sounds typically fall within the range of 12-2000 Hz, which can be shifted to the audible range of 24-4000 Hz by setting R=2. As another example, heart sounds typically fall within the range of 5-200 Hz, which can be shifted to the audible range of 40-1600 Hz by setting R=8. Optionally, practitioner 22 may select the value of R (for example, toggling between preset values for different types of physiological activity) by entering an appropriate user input to stethoscope 20, using the touch screen of display 36, for example.

Stretching the frequency content of this acoustic signal, so as to slow down or accelerate the temporal evolution of a sound without altering its time period, requires an explicit separation of temporal and spectral information. As a result of the spectral interpolation performed at step 62, spectral changes will occur more slowly in the synthesized sound than in the input signal. Simply spacing the frequencies further apart means that phase changes now occur over a longer time interval. Hence, the periodicity of the signal will be inadvertently altered. The solution in the present embodiment is to rescale the phase by precisely the same factor by which the sound is expanded in the frequency domain. This rescaling ensures that the signal in any given filter band has the same frequency variation in the re-synthesis as in the original (though it occurs more slowly), and thus the periodicity of the sounds is preserved.

To carry out the required time domain preservation, digital preprocessing circuit 44 first computes $f_r[n]$, the inverse STFT of $F_r(m,k)$, at an inverse transformation step 64. For this purpose, circuit 44 applies the formula:

$$f_r[n] = \frac{1}{2\pi} \sum_m \sum_k F_r(m,k) * e^{jkn}$$

Circuit 44 then decimates the sequence of time-domain samples $f_r[n]$ by the same factor R as was used in interpolation of the frequency spectrum, at a decimation step 65. The result is a frequency-stretched signal $f_s[n]$, which has the same number of samples, and hence the same periodicity, as the original f[n], but is stretched to higher frequencies. (The decimation performed at step is equivalent to replaying the frequency-shifted sequence of time-domain samples $f_r[n]$ at R times the original sample rate.) DAC 46 converts $f_s[n]$ to analog form, and analog output circuit 48 amplifies and inputs this signal to earphones 30, at an audio output step 66.

The frequency-domain signal $F_r(m,k)$ contains the frequency-stretched spectrum in each of a succession of STFT windows. The interpolation performed at step 62 can add an incoherent phase offset as a function of frequency between successive windows. Therefore, prior to computing the inverse STFT at step 64, circuit 44 typically rotates the peak phase of each frequency component in each time window in order to match the phase in the preceding time window.

Computation and Display of Acoustic Signatures

Figure 4:
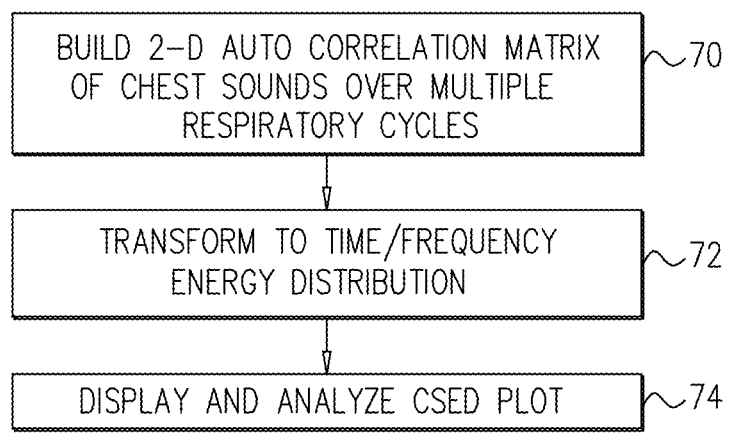
FIG. 4 is a flow chart that schematically illustrates a method for generating an acoustic signature, in accordance with an embodiment of the invention.

FIG. 4 is a flow chart that schematically illustrates a method for generating an acoustic signature, in accordance with an embodiment of the invention. As in the preceding embodiment, the method of FIG. 4 is described here, for the sake of concreteness and clarity, with reference to the components of digital stethoscope 20; but this method may alternatively be implemented in substantially any system that includes a suitable acoustic transducer, display and processing resources.

The method of FIG. 4 makes use of the autocorrelation spectrum of acoustic signals received from microphone 34 over the period of a physiological activity of interest, such as the autocorrelation of heart sounds over the cardiac cycle or breath sounds over the respiratory cycle. For this purpose, it can be useful to extract the period before computing the signature. The period can be extracted from the acoustic signals themselves, using methods that are known in the art. Additionally or alternatively, a motion sensor within case 32, such as accelerometer 41, can be used to sense the respiratory motion of the thorax of patient 24 while head 26 is in contact with the thorax. Processor 50 detects the respiratory motion using the output of the motion sensor and thus extracts the period of the patient's respiratory activity.

The period of the activity, based on the digitized signal x(n) from microphone 34 or accelerometer 41, can itself be computed using the autocorrelation function:

$$y(k) = \frac{\sum_n x(n)x(n+k)}{\sum_n x^2(n)}$$

Processor 50 identifies significant peaks in the autocorrelation y(k), for example, peaks whose amplitudes exceed a certain threshold and are separated by at least a minimum amount of time, such as 0.5 sec for cardiac activity. The time between each pair of successive peaks is taken to be a candidate period. Processor 50 discards outlying values of the candidate period and averages the remaining values to find the actual period for purposes of computing the acoustic signature. Alternatively or additionally, a k-nearest neighbor (KNN) approach can be used in classifying successive periods of the autocorrelation function and thus measure the period accurately.

As noted earlier, this method of identifying the time period of the respiratory activity can be used together with an additional sensor, such as a motion sensor to detect the chest motion.

In the description that follows, the method of FIG. 4 is applied to chest sounds (including infrasonic components) due to respiratory activity, and the resulting acoustic signatures are thus indicative of normal or pathological respiratory patterns. In alternative embodiments, not shown in the figures, the principles of this method can be applied, mutatis mutandis, to cardiac activity. To compute the acoustic signature of the respiratory activity, processor 50 builds a two-dimensional (2D) autocorrelation matrix based on the digitized samples x(n) of the electrical signals from microphone 34, at a matrix construction step 70. The elements of the autocorrelation matrix y(n,l) have the form:

$$y(n,l) = x(n+l)x^*(n-l)$$

In other words, processor 50 computes the autocorrelation as a function of a variable time shift l for each time n within a period of the signal.

Processor 50 transforms the 2D autocorrelation matrix to a matrix representation of the spectral (frequency) distribution of the energy of the acoustic waves over the respiratory period, at a frequency transformation step 72. This step can be carried out by calculating a one-dimensional fast Fourier transform (FFT) over the l-dimension of the autocorrelation matrix, which yields the time/frequency chest sounds energy distribution (CSED):

$$CSED(n, k) = \sum_{l=-N/2}^{\frac{N}{2}-1} y(n, l) e^{-2\pi i k l / N}$$

Here N is the number of samples in a respiratory period. Because it is tied to the actual period of respiration, the CSED provides a consistent representation of the spectral distribution of the energy of the acoustic waves, notwithstanding shifts in time and frequency.

Processor 50 outputs the CSED for used by practitioner 22 and/or further offline recording and analysis, at a CSED output step 74. For example, processor 50 may render a graphical representation of the CSED to display 36 or to a separate, external display (not shown). Typically, this graphical representation comprises a plot having a frequency axis and a time axis, which together define a time-frequency plane. The value of the energy is presented in the plot at each point in the time-frequency plane. A number of modes of display of this sort are shown in the figures that follow.

FIGS. 5A-D are plots that schematically illustrate acoustic signatures, in accordance with an embodiment of the invention. In these pseudo-3D plots, the time-frequency plane is horizontal, and the energy is represented by peaks extending above and below the plane. The time axis is marked in seconds, reflecting the length of an average respiratory period, while the frequency axis is marked in Hertz. The energy scale is relative.

Figure 5A:
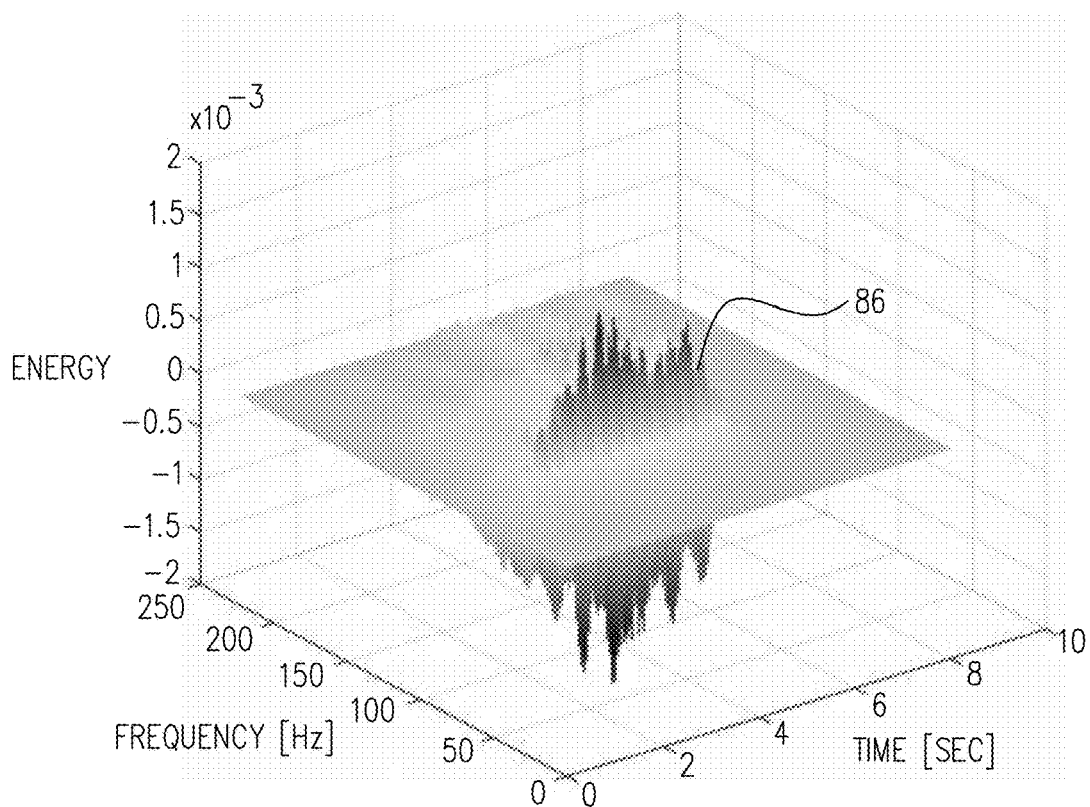
FIGS. 5A-D are plots that schematically illustrate acoustic signatures, in accordance with an embodiment of the invention.
Figure 5B:
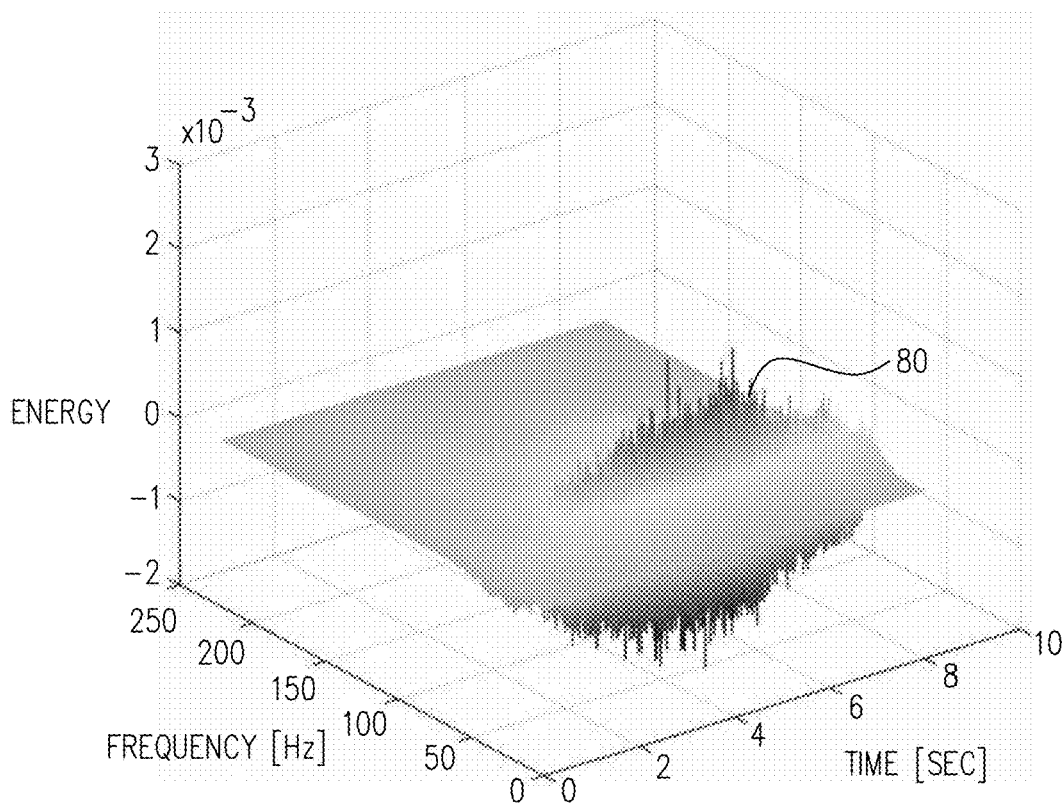

FIG. 5A shows the CSED of normal breath sounds, which is characterized by a sharp ridge 86 of frequencies, in the range of 50-100 Hz, sharp continuously in time over the central part of the respiratory cycle. By contrast, FIG. 5B shows a CSED with a wider, more extended ridge 80, reflecting wheezes in the breath sounds of a patient suffering from bronchiectasis due to cystic fibrosis.

Figure 5C:
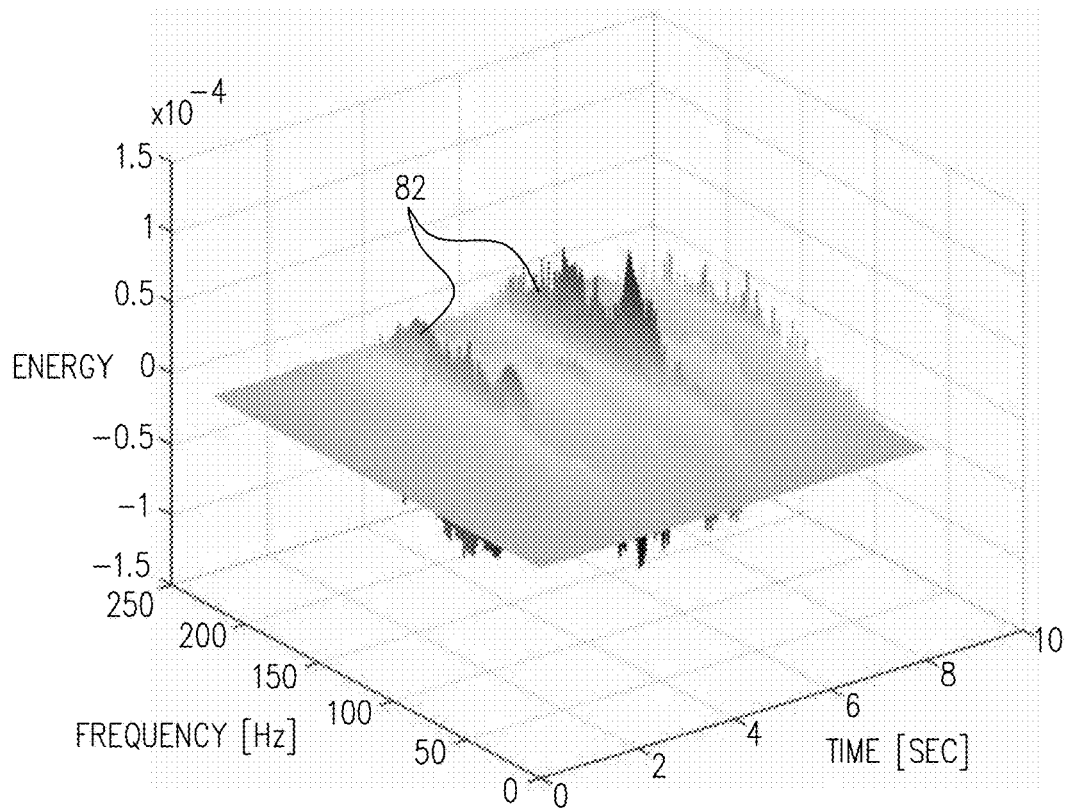
Figure 5D:
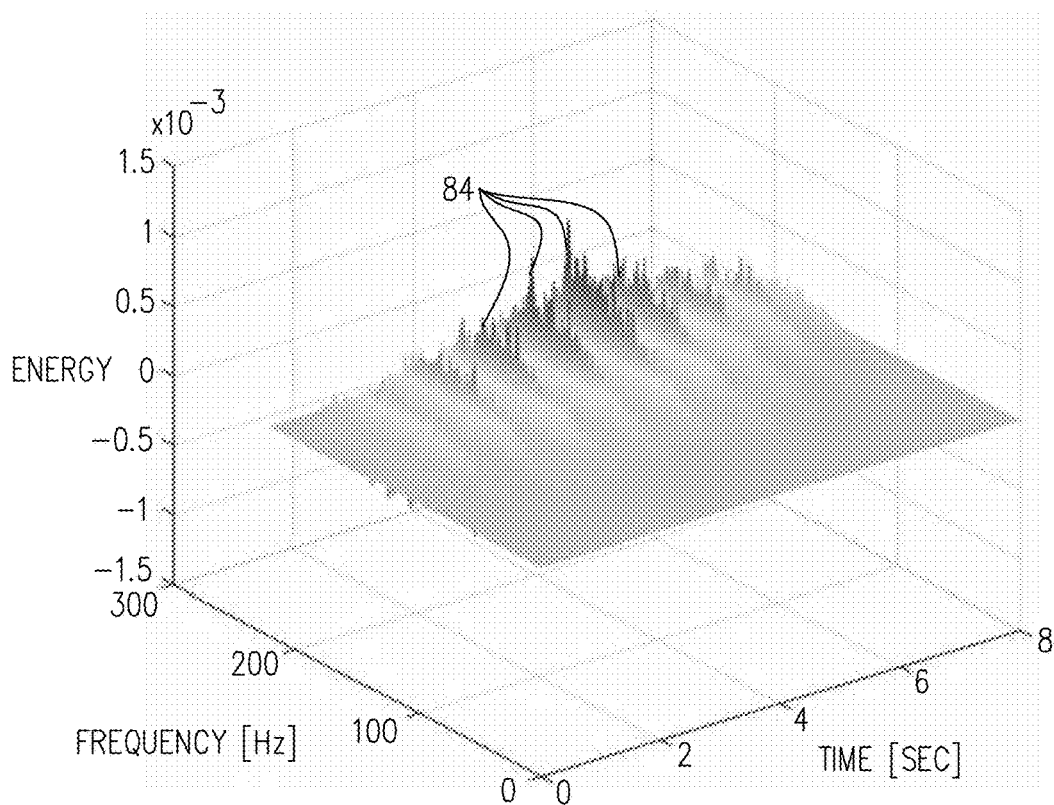
Figure 6A:
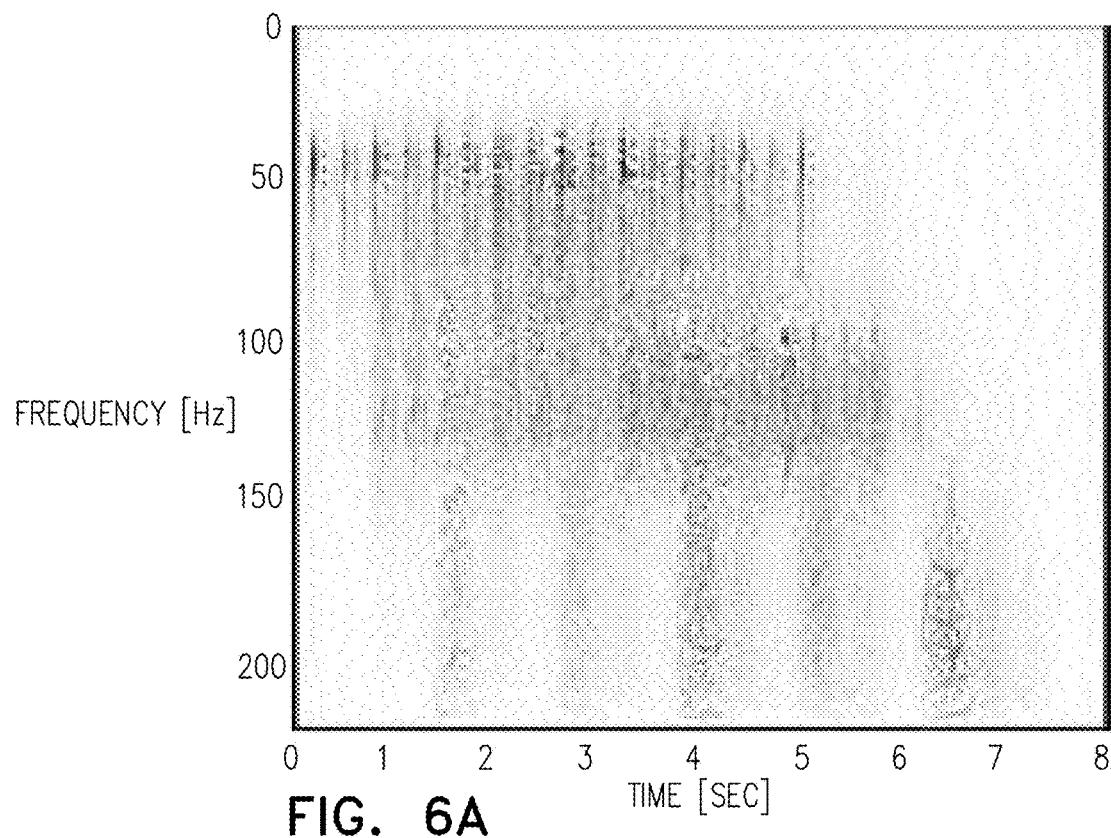
FIGS. 6A-D are plots that schematically illustrate acoustic signatures, in accordance with another embodiment of the invention.
Figure 6B:
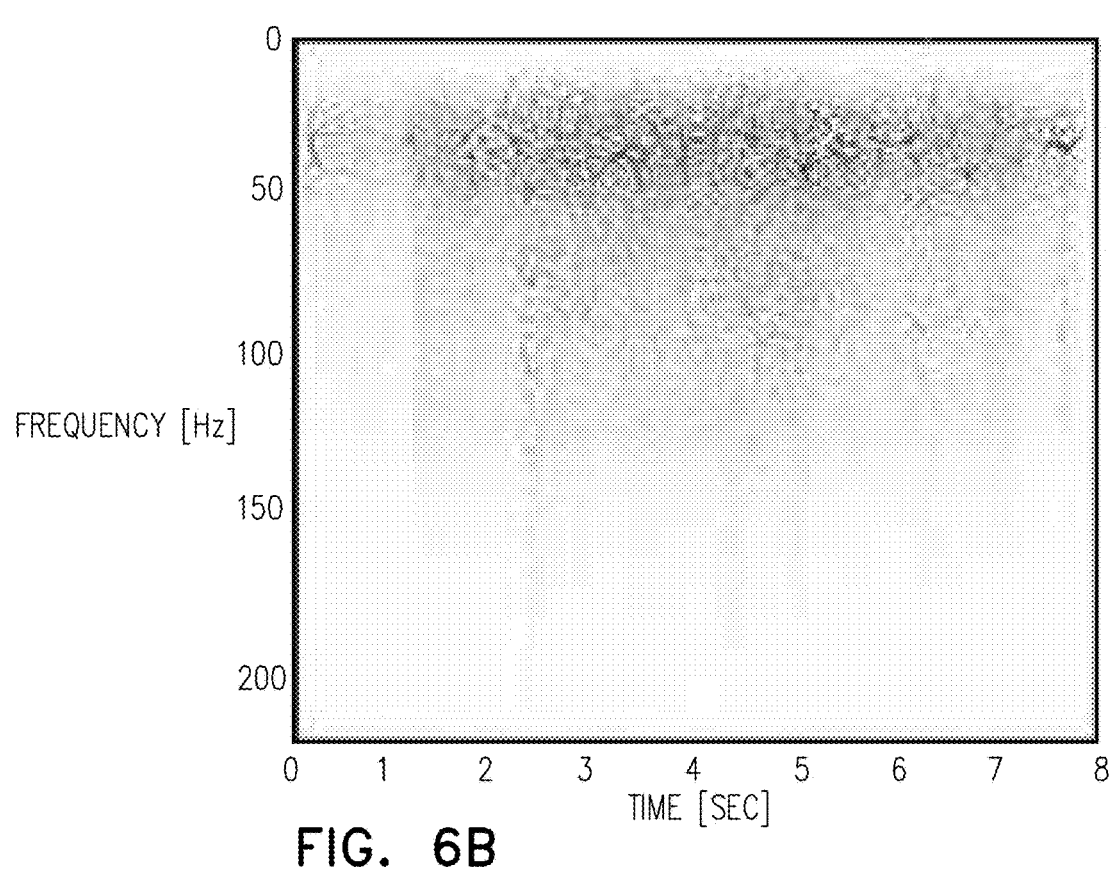
Figure 6C:
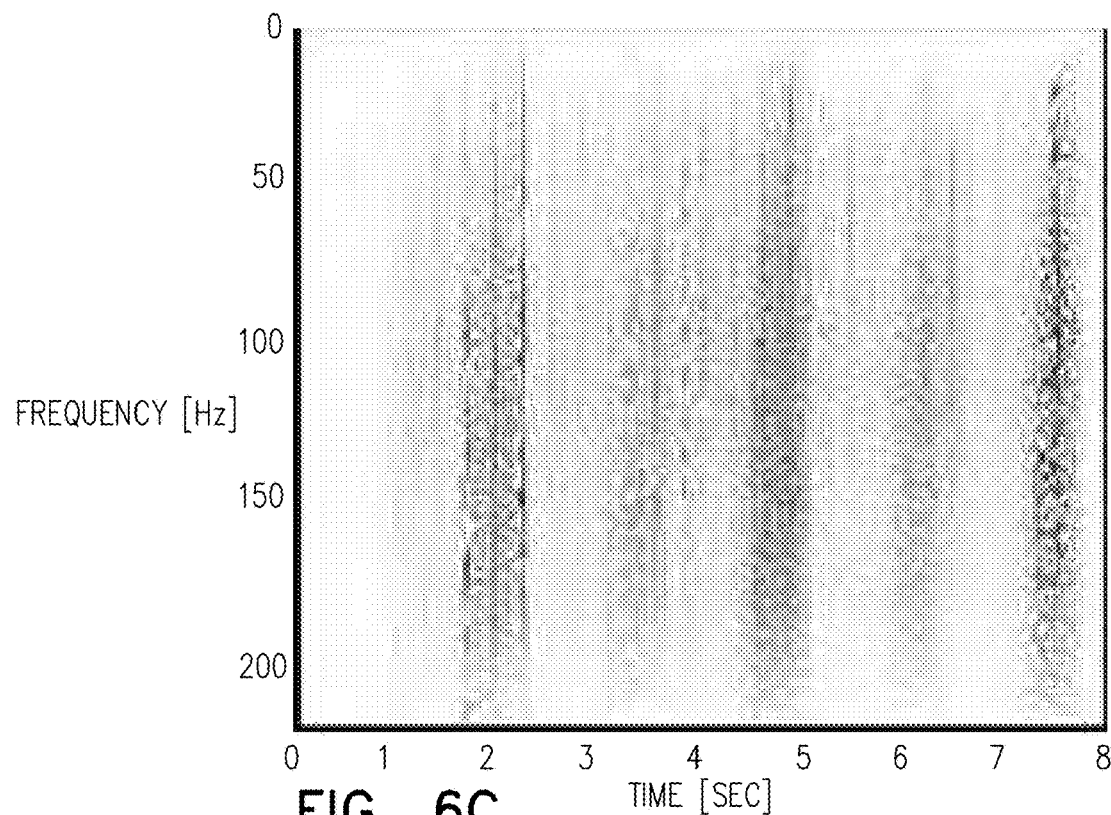
Figure 6D:
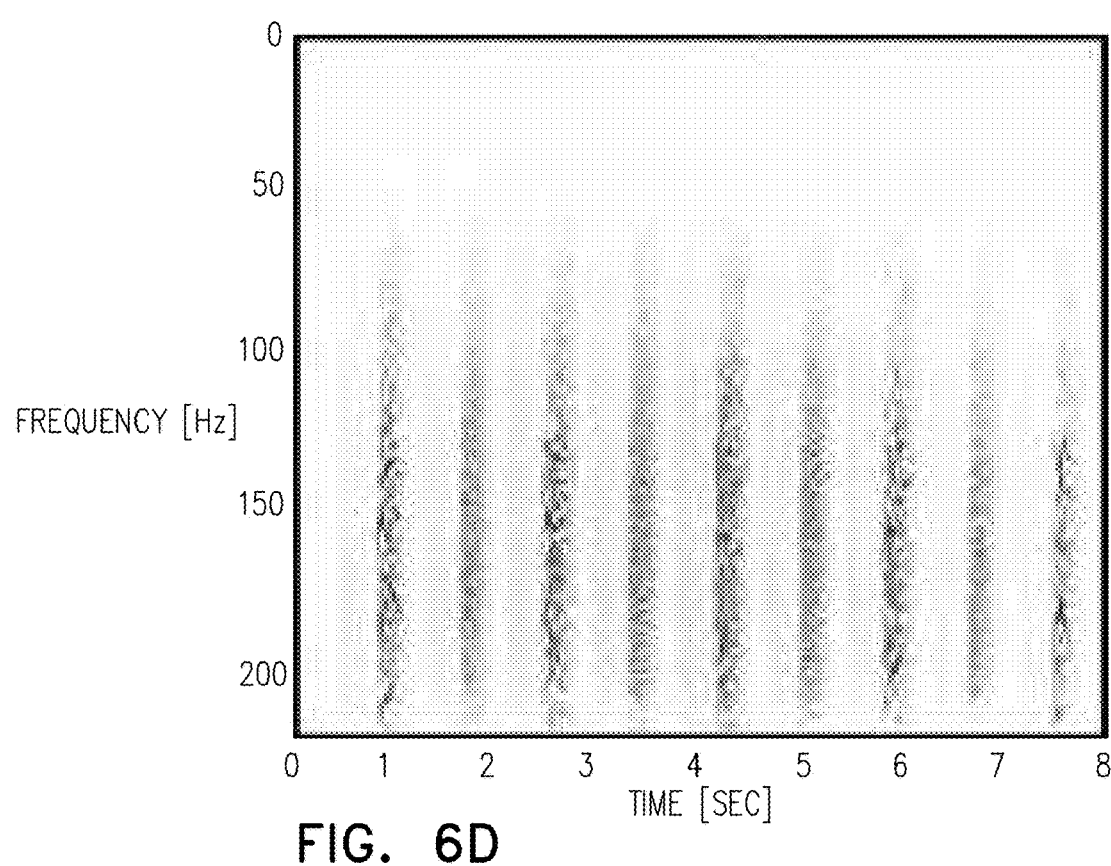

FIGS. 5C and 5D illustrate the effect of crackles in the breath sounds of patients with bronchiectasis and pulmonary edema, respectively. The crackles are reflected in the CSED by ridges 82 and 84 covering wide ranges of frequencies, repeating multiple times over the course of the respiratory cycle.

FIGS. 6A-D are plots that schematically illustrate acoustic signatures, in accordance with another embodiment of the invention. These plots show the same CSED computations, for the same patients, as in FIGS. 5A-D, respectively. In this embodiment, however, the energy as a function of time and frequency is shown as an intensity value, with darker shades of gray corresponding to higher energy values.

Figure 7A:
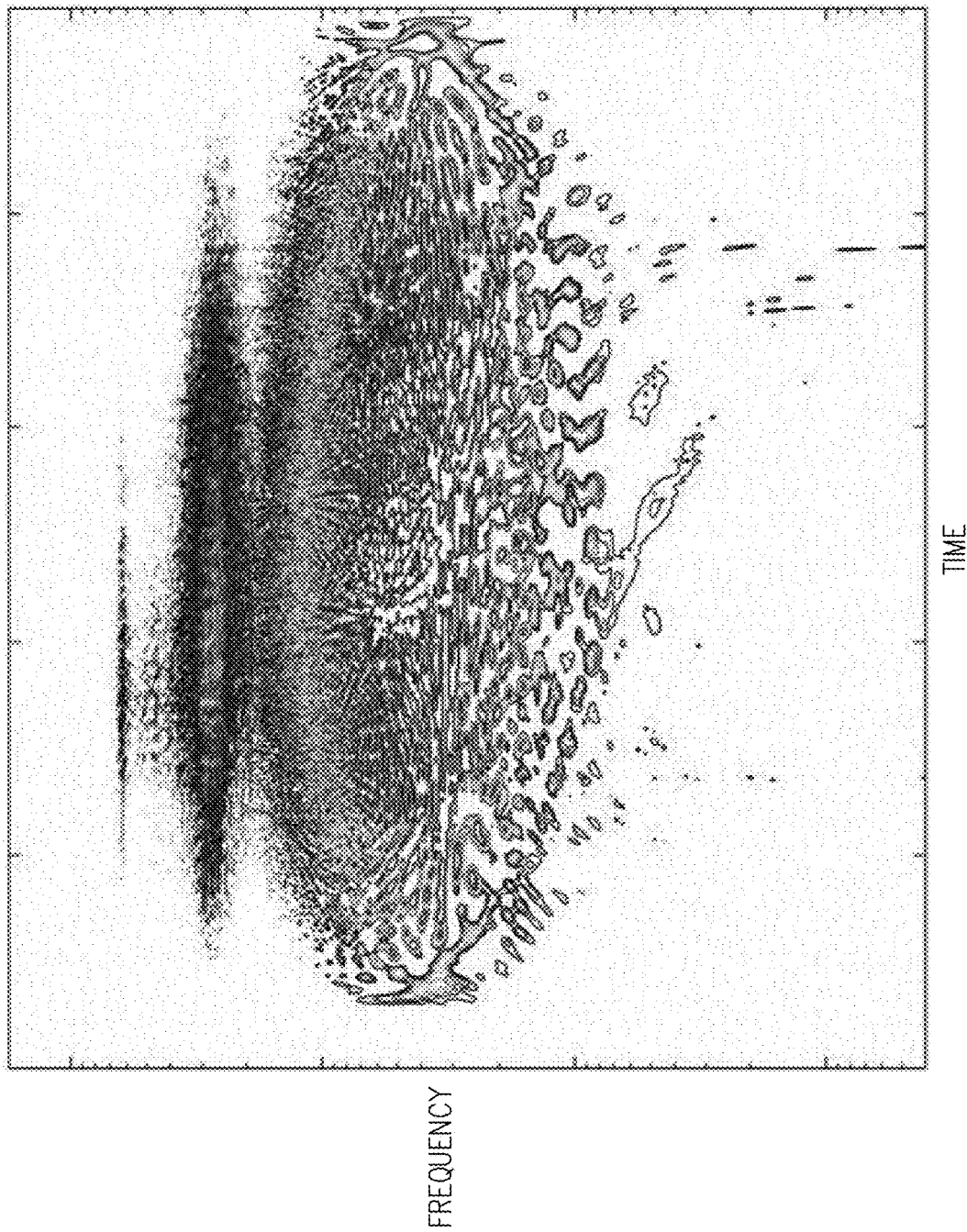
FIGS. 7A-C are plots that schematically illustrate acoustic signatures, in accordance with yet another embodiment of the invention.
Figure 7B:
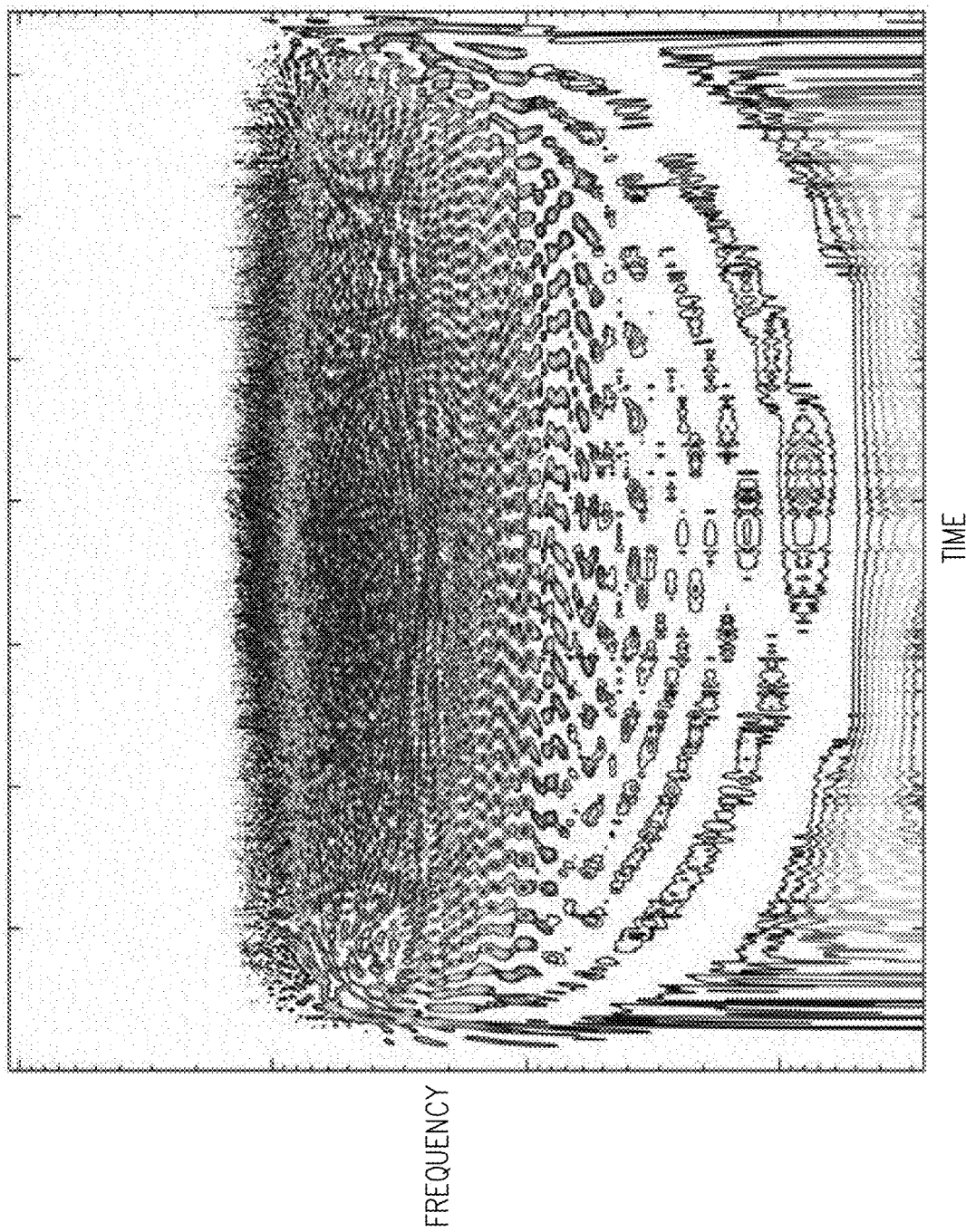
Figure 7C:
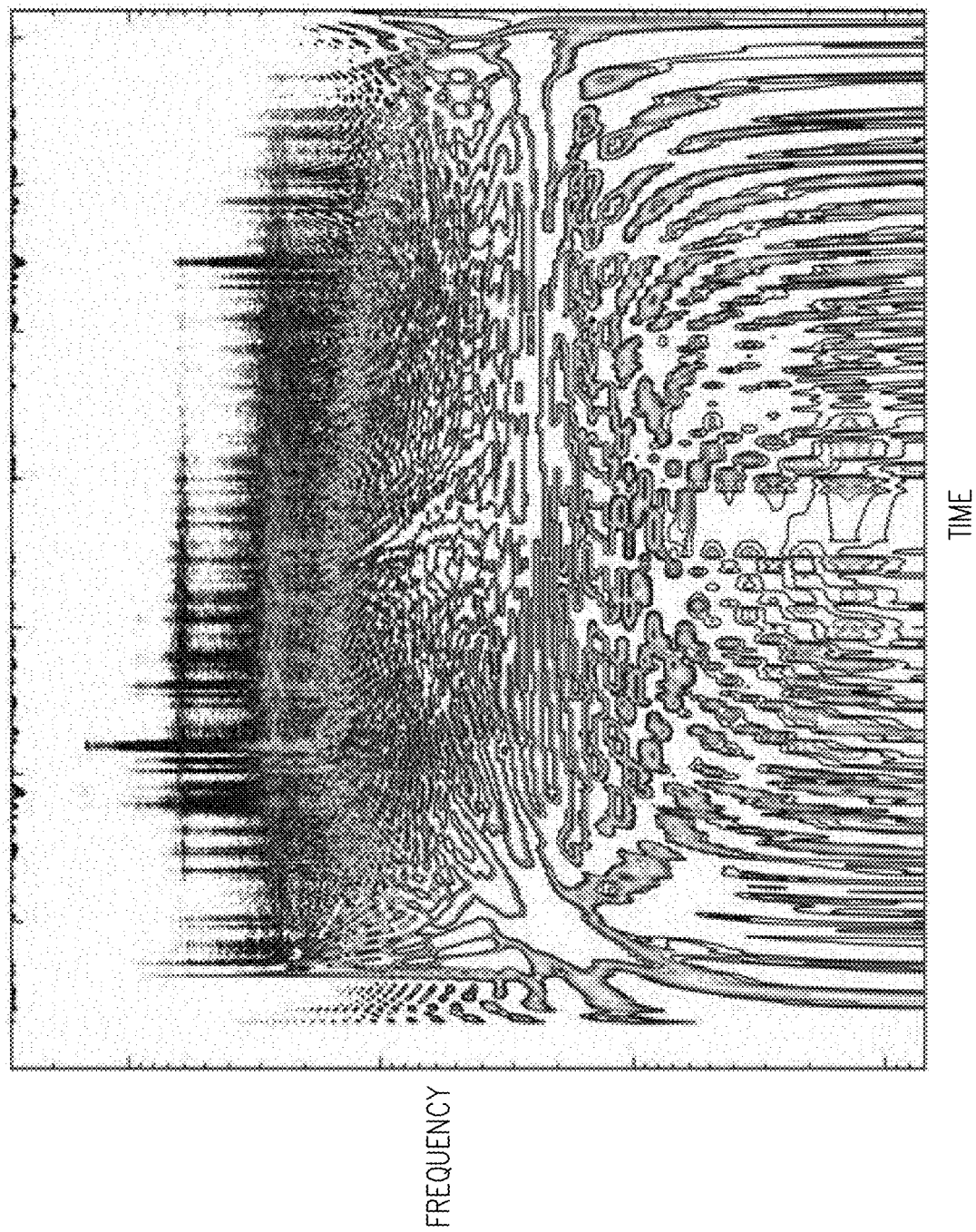

FIGS. 7A-C are plots that schematically illustrate acoustic signatures, in accordance with yet another embodiment of the invention. These plots similarly show energy as an intensity value over the time-frequency plane, except that in this embodiment, the frequency scale is logarithmic.

FIG. 7A shows the company energy spectrum of a normal patient with healthy lungs. By contrast, FIG. 7B shows the CSED computed over the breath sounds of a patient with chronic obstructive pulmonary disease (COPD), with frequency bands extending down to the infrasonic range over the duration of the respiratory cycle. As another example, FIG. 3C shows the CSED of a patient suffering from idiopathic pulmonary fibrosis (IPF), in which crackles are represented by vertical lines in the low-frequency range, again extending down to infrasonic frequencies.

The distinctions between normal respiration and various, specific sorts of pathologies are visually apparent in the acoustic signatures shown above. These acoustic signatures can thus assist the practitioner in making fast, accurate diagnoses and assessing changes in the patient's condition thereafter.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical device, comprising:
   an acoustic transducer, which is configured to sense infrasonic waves emitted from a body of a living subject and to output an electrical signal in response to the sensed waves, wherein the infrasonic waves have a periodicity due to a periodic physiological activity in the body;
   at least one speaker, which is configured to output audible sounds in response to an electrical input; and
   processing circuitry, which is configured to process the electrical signal over a succession of time windows so as to generate, in real time, a frequency-stretched signal in which infrasonic frequency components of the electrical input are shifted to audible frequencies while preserving the periodicity of the periodic physiological activity in the frequency-stretched signal, and to input the frequency-stretched signal to the at least one speaker,
   wherein the processing circuitry is configured to receive and digitize the electrical signal, to transform the digitized signal to a frequency domain, to shift the infrasonic frequency components to the audible frequencies by interpolating the transformed signal in the frequency domain by a given factor so as to generate a frequency-shifted transformed signal, to retransform the frequency-shifted transformed signal to a time domain, and to decimate the retransformed signal in the time domain by the given factor in order to generate the frequency-stretched signal while preserving the periodicity of the periodic physiological activity.

2. The device according to claim 1, and comprising a user interface, which is configured to receive a user input from a user of the device indicative of a desired stretch of the infrasonic frequency components, and wherein the processing circuitry is configured to adjust the factor responsively to the user input.

3. The device according to claim 2, wherein the user interface is configured to select a value of the factor from among a first value for transformation of respiratory sounds and a second value, greater than the first value, for transformation of cardiac sounds.

4. The device according to claim 1, wherein the processing circuitry is configured to stretch the infrasonic frequency components so that a component at 5 Hz is shifted to a frequency of at least 20 Hz.

5. The device according to claim 1, and comprising a case, which contains the acoustic transducer and at least a part of the processing circuitry, and which is configured to be brought into contact with the body of the living subject,
wherein the at least one speaker comprises earphones extending from the case and configured to configured to output the audible sounds.

6. The device according to claim 1, wherein the processing circuitry is configured to transform the digitized signal to the frequency domain by computing a short-time Fourier transform (STFT) over each of the time windows, while applying a window function to the digitized signal.

7. The device according to claim 1, wherein the processing circuitry is configured to rotate a phase of the decimated retransformed signal in each of the time windows in order to match the phase of a preceding time window in the succession.

* * * * *